United States Patent [19]

Lange, III et al.

[11] Patent Number: 5,063,210
[45] Date of Patent: Nov. 5, 1991

[54] USE OF SULFATED POLYSACCHARIDES TO DECREASE CHOLESTEROL AND FATTY ACID ABSORPTION

[76] Inventors: Louis G. Lange, III, 38 Kingsbury Place, St. Louis, Mo. 63112; Curtis A. Spilburg, 2230 Willow Ridge La., Chesterfield, Mo. 63017

[21] Appl. No.: 429,398

[22] Filed: Oct. 31, 1989

Related U.S. Application Data

[63] Continuation-in-part of Ser. No. 340,868, Apr. 20, 1989.

[51] Int. Cl.$^5$ .............. A61K 31/715; C12N 9/16
[52] U.S. Cl. ..................................... 514/54; 514/55; 514/57; 514/59; 536/118; 536/122; 435/196
[58] Field of Search ............ 514/54, 55, 57, 59; 536/53, 20, 30, 51, 118, 122; 424/439; 426/658; 435/196

[56] References Cited

U.S. PATENT DOCUMENTS

| | | | |
|---|---|---|---|
| 3,148,114 | 9/1964 | Fahrenbach et al. | 514/54 |
| 3,175,942 | 3/1965 | Anderson et al. | 514/54 |
| 3,511,910 | 5/1970 | Halleck | 514/54 |
| 3,627,872 | 12/1971 | Parkinson | 514/57 |
| 4,066,829 | 1/1979 | Nair et al. | 536/103 |
| 4,150,110 | 4/1979 | Yoshida et al. | 424/81 |
| 4,160,826 | 7/1979 | Fischetti | 514/59 |
| 4,223,023 | 9/1980 | Furda | 514/55 |
| 4,436,731 | 8/1984 | Maltz | 536/20 |
| 4,520,017 | 5/1985 | Tunc | 536/5 |
| 4,602,003 | 7/1986 | Malinow | 536/5 |
| 4,623,539 | 11/1986 | Tunc | 514/56 |
| 4,727,063 | 2/1988 | Naggi et al. | 514/56 |
| 4,883,788 | 11/1989 | Day et al. | 514/57 |

FOREIGN PATENT DOCUMENTS

| | | |
|---|---|---|
| 0241299 | 11/1959 | Australia . |
| 0053473 | 6/1982 | European Pat. Off. . |
| 116801 | 8/1984 | European Pat. Off. . |
| 125152 | 11/1984 | European Pat. Off. . |
| 84400438.2 | 11/1984 | European Pat. Off. . |
| 129748 | 1/1985 | European Pat. Off. . |
| 84402495.0 | 7/1985 | European Pat. Off. . |
| 184480 | 6/1986 | European Pat. Off. . |
| 189696 | 8/1986 | European Pat. Off. . |
| 87114497.8 | 8/1988 | European Pat. Off. . |
| 1492011 | 4/1962 | Fed. Rep. of Germany . |
| 1916535 | 7/1962 | Fed. Rep. of Germany . |
| 49-43937 | 11/1974 | Japan . |
| 55-15435 | 2/1980 | Japan . |
| WO88/06037 | 8/1988 | PCT Int'l Appl. . |
| 871590 | 6/1961 | United Kingdom . |
| 896876 | 5/1962 | United Kingdom . |
| 953626 | 3/1964 | United Kingdom . |
| 1053143 | 12/1966 | United Kingdom . |
| 1164569 | 9/1969 | United Kingdom . |
| 1344727 | 1/1974 | United Kingdom . |
| 1433732 | 4/1976 | United Kingdom . |
| 2055872 | 3/1981 | United Kingdom . |
| 2068371 | 8/1981 | United Kingdom . |
| 2078768 | 1/1982 | United Kingdom . |

OTHER PUBLICATIONS

Hoffman et al., Carbohydrate Polymers, "Studies on the Blood-Anticoagulant Activity of Sulphated Polysaccharides with Different Uronic Acid Content" (1982) 2:115-121.

Fernandez et al., Biochim. Biophys. Acta, "Effects of Tetrahydrolipstatin, A Lipase Inhibitor, on Absorption of Fat From the Intestine of the Rat" (1989) 1001:249-255.

Ogawa et al., Chem. Pharm. Bull., "Studies of Hypolipidemic Agents. I. Syntheses and Hypolipidemic Activities of 1-Substituted 2-Alkanone Derivatives" (1986) 34:1118-1127.

"Studies on Hypolipidemic Agents, IV, Synthesis and Biological Activities of Trans- and Cis-2-(4-Alkylcy- (List continued on next page.)

*Primary Examiner*—Johnnie R. Brown
*Assistant Examiner*—Nancy S. Carson
*Attorney, Agent, or Firm*—Allegretti & Witcoff, Ltd.

[57] ABSTRACT

This invention encompasses a method and compositions which inhibit pancreatic cholesterol esterase and triglyceride lipase and hence, lower cholesterol and triglycerides in the blood stream.

4 Claims, 3 Drawing Sheets

OTHER PUBLICATIONS clohexyl)-2-oxoethyl Arenesulfonates" 1987 35:3276-3283.

"Studies on Hypolipidemic Agents. V. Synthesis and Esterase-Inhibitory Activity of 2-14,-and 4,4-Dialkylcyclohexyl)-2-oxoethyl Arenesulfonates" (1987) 35:413-4136.

Morin et al., Biochim. Biophys. Acta, "Relative Specificities of Inhibition of Acid Cholesteryl Ester Hydrolase and Neutral Cholesteryl Ester Hydrolase in Cultured Rabbit Aortic Smooth Muscle Cells by Esterastin and Cholesteryl Oleyl Ether" (1989) 1004:139-142.

Seethanathan et al., Molecular & Cellular Biochem., "Glycosaminoglycans from Ateroid and Bovine Duodenal Mucosa and Pancreas" (Sep. 30, 1975) 8:177-183.

Hadvary P., et al., Int. J. Obesity, "Lipstatin and Tetrahydrolipstatin, Potent and Selective Inhibitors of Pancreatic Lipase" (1987) 11: Suppl. 2,21.

Proceedings of the Journal of Experimental Biology and Medicine, 116: 496 (Vahouny and Treadwell, 1964).

Archives of Biochemistry and Biophysica 168: 57-65 (Calame et al., 1975).

Biochemica et Biophysica Acta, 296: 94-104 (Van Den Bosch et al., 1973).

Biochemica et Biophysica Acta 486: 103-113 (Momsen and Brockman, 1977)

European Journal of Biochemistry 117: 457-460 (Guy et al., 1981).

Biochemical and Biophysical Research Communications 134: 386-392 (Sutton et al., 1986).

Arch. Int. Pharmacodyn. 144: 1-19 (Cook et al., 1963).

Proc. Natl. Acad. Sci, U.S.A. 85: 7438-7442 (Bosner, et al., 1988).

Carbohydrate Research 73: 332-336 (Larm et al., 1979).

Clinical Research 37: 366A (Bosner et al., 1989).

Am. J. Physiol. 206: 223-228 (Borja et al., 1964).

"Agents Used to Treat Hyperlipidemia", The AMA Drug Evaluations, 6th Ed., pp. 903-926.

Journal of the American Medical Association 253: 2080-2085 (1985).

Journal of the American Medical Associates 253: 2087-2090 (Harlan and Stross, 1985).

Journal of the American Medical Association 253: 2091-2093 (Kronmal, 1985).

Journal of the American Medical Association 253: 2094-2095 (Rahimtoola, 1985).

Arch. Intrn. Med., 148: 36-69 (1988).

American Journal of Surgery 113: 27-31 (Barnes et al., 1967).

Journal of Clinical Biochemical and Nutrition 2: 55-70 (Goto et al., 1987).

Jansen et al, Biochem. Biophys. Res. Commun, 92(1):53-59 (1980).

Superko; Cardiovascular Reviews and Reports, 6(11):1253-1254, 1257-1258 and 1263-1265 (1985).

Isakson et al.; Digestion 24:54-59 (1982).

Hansen et al., Hepato-Gastroenterol, 29:157-160 (1982).

USE OF SULFATED POLYSACCHARIDES TO DECREASE CHOLESTEROL AND FATTY ACID ABSORPTION

This application is a continuation-in-part application of pending U.S. Pat. Application Ser. No. 07/340,868, filed on Apr. 20, 1989.

BACKGROUND OF THE INVENTION

This invention relates to a method for decreasing intestinal cholesterol and fatty acid absorption in man and, specifically, to inhibiting or decreasing intestinal cholesterol and fatty acid absorption by oral administration of synthetic sulfated polysaccharides which inhibit pancreatic cholesterol esterase. The invention is based upon our discovery of sulfated polysaccharides which are potent inhibitors of human pancreatic cholesterol esterase, the enzyme responsible for promoting the intestinal absorption of cholesterol and fatty acids derived from their esterified dietary forms. The invention is also based on our observation that such agents are stable and are bioavailable to the intestine when delivered in baked goods such as biscuits and can therefore be administered in food products.

Atherosclerosis is the leading cause of death in the United States and high serum cholesterol concentrations are associated with increased risks of fatal atherosclerosis events, *J.A.M.A.*, 53 2094 (1985) (NIH Consensus Panel). In 1988. a Consensus Panel of experts at the National Institute of Health stated that a major public health priority was the reduction of cholesterol, and that the goal of front line therapy should be to diminish the intestinal absorption of cholesterol, either through eating less cholesterol or through the use of drugs which act in the intestine to reduce cholesterol levels, *Arch Inst. Med.*, 148, 36 (1988) (Consensus Full Report). Currently, the principal drug to inhibit cholesterol absorption is cholestyramine, a bile acid sequesterant. "Agents to Treat Hyperlipidemia", *The AMA Drug Evaluations*, 6th Ed., p. 903. This agent binds bile salts within the intestinal lumen, and the resulting complex is excreted in the feces. Since bile acid is not reabsorbed, the liver uses additional cholesterol to synthesize more bile which effectively lowers the sterol concentration in the body. Bile salt sequesterants are effective in lowering cholesterol, but they seldom reduce serum cholesterol by more than 15%, and they are poorly tolerated by patients. Large quantities of these ion exchange resins must be ingested (15g or more), which lead to assaults on both the gustatory senses and intestinal function. Common side effects are constipation and bloating *J.A.M.A.*, 253. 2095 (1985).

Cholesterol esterase is secreted by the pancreas after eating and is active in hydrolyzing ingested dietary esters of cholesterol. The enzyme is essential for absorption of cholesterol. If enzyme activity is removed from pancreatic juice, no cholesterol absorption occurs. If the cholesterol esterase activity is returned, absorption of cholesterol occurs. Borja et al., *Am. J. Physiol.*, 206. 223 (1964) and Vahouny and Treadwell; *Proc. J. Exp. Biol. and Med.*, 116, 496 (1964). In man, the 100 kiloDalton (kDa) molecular weight protein responsible for hydrolyzing cholesterol esters is also the principal triglyceride lipase in the pancreas. Bosner, et al., *Clin. Res.*, 37, 366A (1989). Since fatty acids are also important in the genesis of atherosclerosis, the enzyme cholesterol esterase is essential in the intestinal absorption of those lipids responsible for producing atherosclerosis.

Despite this key role and the stated mission of the NIH to target strategies of diminishing cholesterol absorption from the intestine, no systematic study of inhibition of human pancreatic cholesterol esterase has been performed. In fact, few studies have focused on the human enzyme at all, with most attention directed to other mammalian enzymes (rat, pig, and cow) Calame et al., *Arch. Biochem. Biophys.*, 168, 57 (1975); Van den Bosch et al., *Biochem. Biophys. Acta.*, 286, 94 (1973); Momsen et al., *Biochem. Biophys. Acta.*, 486, 103 (1977); Guy et al., *Eur. J. Biochem.*, 117, 457 (1981); and Sutton et al., *Biochem. Biophys. Res. Commun.*, 134, 386 (1986). Thus, there has been an important and continuing need to discover inhibitors of human pancreatic cholesterol esterase. The pharmacology of various sulfated polysaccharides has been investigated. Cook and Cammarata, *Arch. Intern. Pharmacodyn.*, 144, 1 (1963). In particular, sulfated amylopectin has been taught in U.S. Pat. No. 4,150,110 as an antiulcer agent, but its properties as a cholesterol esterase inhibitor, which decrease absorption of cholesterol, have not been recognized. Sulfated dextran has been identified as an antiulcer agent, *Am. J. Surgery*, 113, 27 (1967). This compound has been recognized for use in the treatment of hyperlipemia and as an orally administered anticoagulant, British Patent No. 953,626. In addition, certain sulfated dextrans, specifically those of low molecular weight (7000-8000, 7-8 kDa), have been shown to reduce serum cholesterol levels at a dose of 1800 mg/day. Goro et al., *J. Clin. Biochem. Nutr.* 2:55-70 (1987).

SUMMARY OF THE INVENTION

The present invention is directed to compounds and methods for decreasing intestinal absorption of cholesterol and fatty acid by inhibiting human pancreatic cholesterol esterase, a key enzyme involved in mediating absorption, by orally administering sulfated polysaccharides having molecular weights greater than 10 kDa in an amount effective for inhibiting cholesterol esterase.

DESCRIPTION OF THE PREFERRED EMBODIMENTS

Figure 1:
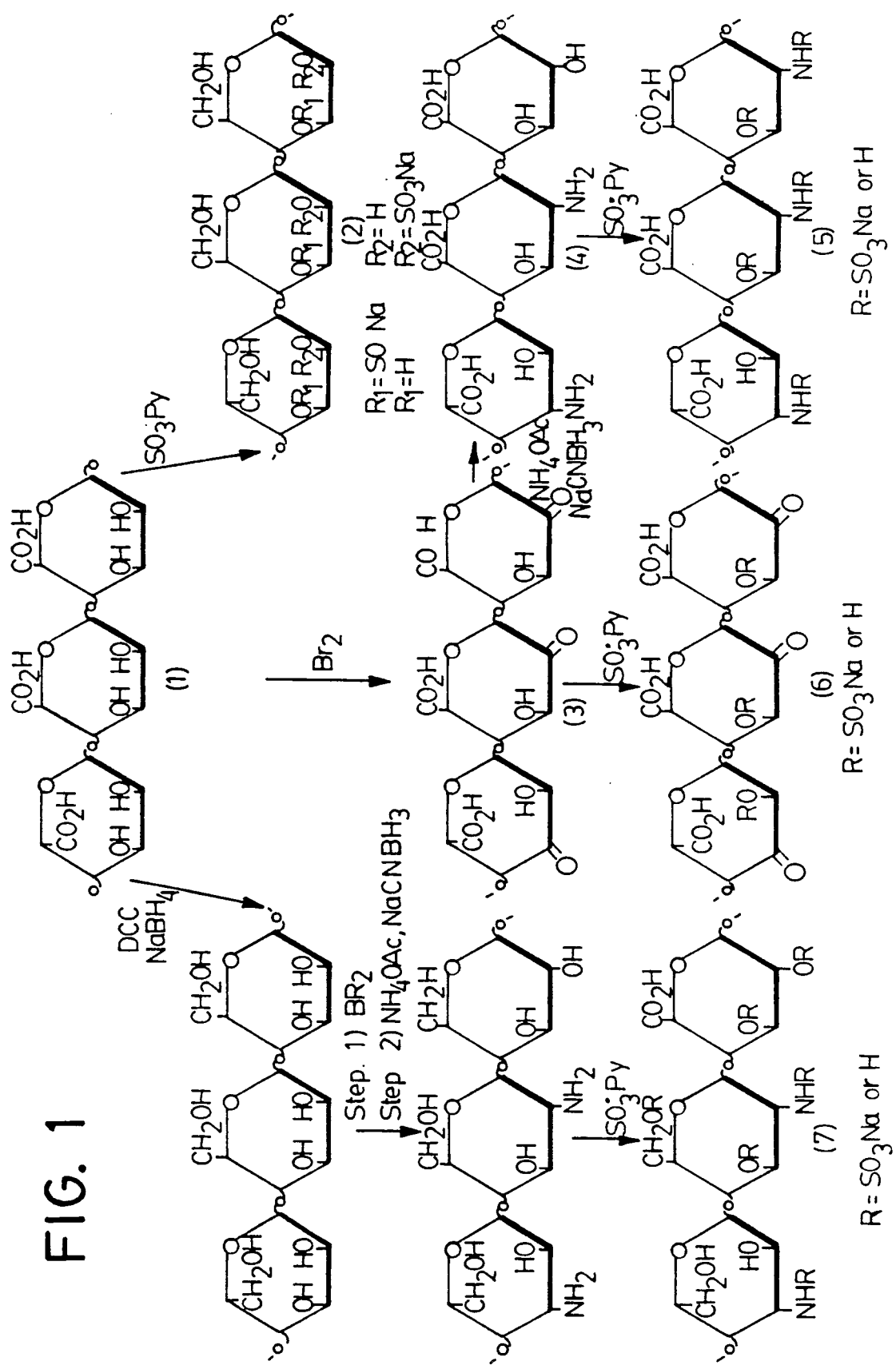
FIG. 1. The synthetic strategy for preparing several sulfated alginic acid derivatives.

In accordance with the present invention, we have made certain discoveries concerning structural features of sulfated polysaccharide inhibitors of human pancreatic cholesterol esterase, including discoveries as to the synthesis and characteristics of sulfated polysaccharides that render highly specific derivatives with subnanomolar inhibitory constants.

Low molecular weight sulfated dextran has been used to reduce serum cholesterol levels. Goro et al., *J. Clin. Biochem. Nutr.*, 2:55-70 (1970). The molecular weight of this sulfated dextran is between 7-8 kDa. This low molecular weight allows the sulfated dextran to be absorbed by the gastrointestinal system. Absorbtion of the sulfated dextran may contribute to various side effects as well as decreased efficacy. In addition, this dextran is randomly sulfated at various positions of the polysaccharide.

Increased inhibitory activities are realized from increased molecular weight and sulfation at a specific position; increased efficacy is obtained by reducing absorbtion of the polysaccharides. Accordingly, the present invention includes non-absorbable sulfated polysaccharides having a molecular weight greater than 10,000 (10 kDa) for use in inhibiting the activity of cholesterol esterase. The present invention is also directed to sulfated polysaccharides which are sulfated in a controlled manner at the 3-position.

Our investigations indicated that a variety of polysaccharide polymers that exist in nature can be sulfated to produce potent inhibitors of human pancreatic cholesterol esterase. Thus, we have reacted in a controlled manner a variety of abundant and cheap polysaccharides such as alginic acid (from seaweed), pectin (from vegetables and fruit), chitin and chitosan (from mollusks), and dextrans and cellulose (from plants and trees) to produce sulfated derivatives. These derivatives are all water soluble, potent inhibitors of human pancreatic cholesterol esterase, whereas the parent starting polymers are either not inhibitory or poorly inhibitory. In addition, sulfated amylopectin is an effective inhibitor of cholesterol esterase. Amylopectin sulfate and its uses as a pharmaceutical agent is described in U.S. Pat. Nos. 4,150,110 and 4,066,829. The use of dextran sulfate as a pharmaceutical agent is discussed in *Am. J. Surgery*, 113, 27 (1967). These disclosures are incorporated herein by reference.

to inhibit the absorbance of cholesterol. The increased molecular weight also increases the inhibitory activity of the polysaccharides. For example, dextran sulfate of molecular weight 5000 (5 kDa) exhibited an $IC_{50}$ of 20 nM, while the $IC_{50}$ of 500,000 molecular weight (500 kDa) dextran sulfate was 0.02 nM.

Accordingly, the present invention includes compounds of the formulas:

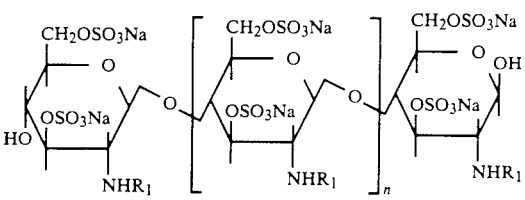

having a molecular weight greater than 10 kDA and wherein $R_1$ is $-COCH_3$ or $-SO_3Na$,

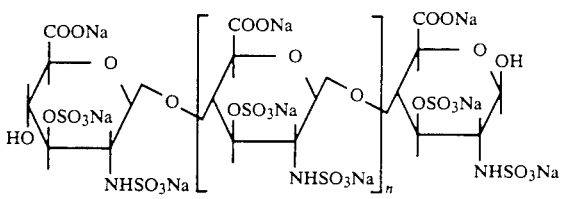

having a molecular weight greater than 10 kDa

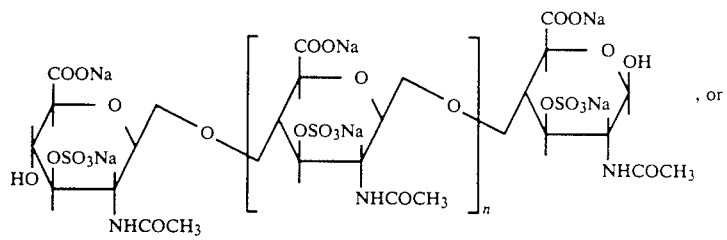

, or having a molecular weight greater than 10 kDa.

Furthermore, agar, after extraction from algae and sulfation, is an extremely potent inhibitor of human pancreatic cholesterol esterase. Agar is a linear polysaccharide composed of alternating D-galactose and 3, 6 anhydro-L-galactose units. Treatment of commercial gum agar results in a gel which is soluble in water. This aqueous solution inhibits human cholesterol esterase with an $IC_{50}$ of $3.3 \times 10^{-11}$M (assuming a molecular weight of 300kDa). Native agar, in contrast, is a much weaker inhibitor of human cholesterol esterase, having an $IC_{50}$ of $3 \times 10^{-8}$M. This inhibition may be due to the presence of agaropectin, a sulfated form of agar which contaminates most commercial preparations of agar.

While a number of structural features can modulate the degree of inhibition, the presence of a 3-sulfate markedly enhances inhibition. The presence of a 3-sulfate on the sugar ring is both necessary and sufficient for producing inhibitory activity in various polysaccharides toward human pancreatic cholesterol esterase. However, the presence of a 2-sulfate decreases inhibition while a 6-sulfate is unnecessary.

The efficacy of sulfated polysaccharides for decreasing absorbance of cholesterol is increased by reducing the absorbtion of the sulfated polysaccharide. High molecular weight sulfated polysaccharides are non-absorbable and, therefore, are necessary and sufficient In essence, our discovery leads to a practical method for converting naturally occurring polysaccharide polymers often regarded as waste to a series of high potent, cheap, non-absorbed and non-toxic inhibitors of cholesterol and fatty acid absorption that can be administered as a soluble agent in small and well-tolerated quantities.

These sulfated polysaccharide inhibitors of cholesterol esterase can be administered in pharmaceutical dosage forms such as tablets, capsules, liquids, and powders. They also can be incorporated with food products such as biscuits and cookies. In essence, sulfated polysaccharides can be used as a dietary supplement to reduce cholesterol and fatty acid absorption. Those skilled in the food and pharmaceutical arts will recognize a wide variety of formulations and vehicles for administering sulfated polysaccharides. Preferably, sulfated polysaccharides are administered with food or about the time of food intake.

Moreover, these sulfated polysaccharide inhibitors of cholesterol esterase can be administered in combination with cholesterol synthesis blockers. Patients treated with cholesterol synthesis blockers experience various toxic side effects. This toxicity can be reduced by decreasing the dose of cholesterol synthesis blocker administered to the patient. Therefore, administering the sulfated polysaccharides of the present invention in combination with drugs that are absorbed by the gastrointestinal tract and block the endogenous biosynthesis of cholesterol allows for decreased dosages of cholesterol synthesis blockers to obtain the same end result. The toxicity associated with cholesterol synthesis blockers can be effectively reduced while still reducing serum cholesterol levels.

Persons having skill in the art will recognize various cholesterol synthesis blockers, such as, for example, lovastatin, which can be combined with the sulfated polysaccharides of the present invention to reduce serum cholesterol levels.

The invention is illustrated further by the following examples which are not to be construed as limiting the invention in scope or spirit to the specific procedures described in them.

EXAMPLE I

Alginic acid from *Macrocystis pyrifera* (kelp) was dissolved in water at a concentration of 1 mg/ml. This stock solution was used to prepare various polysaccharide concentrations down to $10^{-5}$ mg/ml. Human pancreatic cholesterol esterase was purified as described by Bosner et al., *Proc. Nat'l. Acad. Sci.*, 85, 7438 (1988). To measure cholesterol esterase inhibition by alginic acid, 50 µl of cholesterol esterase (10 µg/ml), 75 µl of phosphatidylcholine vesicles containing cholesteryl $^{14}$C-oleate (1 mM 2,000 CPM/nmole), 25 µl of 100 mM taurocholate, 120 µl of 150 mM Tris, pH 7.5 and 30 µl of test alginic acid solution were incubated at 37° C. for fifteen minutes. The assay was quenched by placing the reaction vessels in a 4° C. ice bath and by adding 0.6 ml of 0.3 N NaOH and 3 ml of benzene/chloroform/methanol (1.0/1.2/0.5). The quenched reactions were vortexed for 30 seconds, centrifuged at 3,000 g for 15 minutes and 1 ml of the upper aqueous phase was added to 7 ml of Aquasol-2 (DuPont) with 0.025 ml of 6 N HCl. These mixtures were vortexed for one minute and counted for $^{14}$C-oleate. The counts were compared to a sample which contained cholesterol esterase but no alginic acid to determine the percentage of inhibition.

Figure 2:
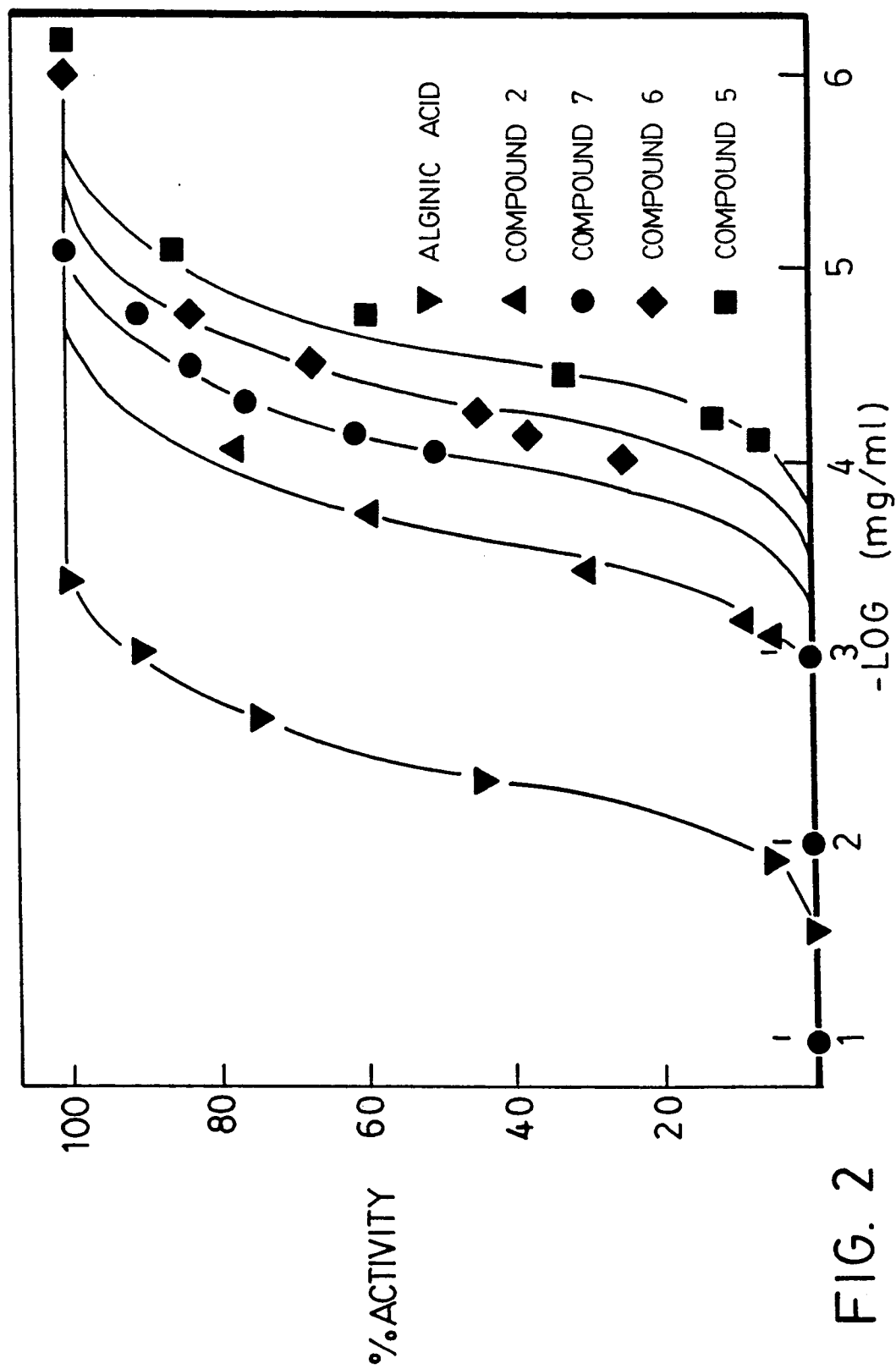
FIG. 2. Inhibition of human cholesterol esterase (100 kDa) by various sulfated alginic acid derivatives.

Following this assay procedure, alginic acid was tested for inhibition from $10^{-1}$ mg/ml to $10^{-4}$ mg/ml. As shown in FIG. 2, this polysaccharide had an $IC_{50}$ of 4 µg/ml or 20 nM (assuming a molecular weight 240 kDa).

EXAMPLE II

Sulfation of alginic acid markedly enhances its inhibitory ability, as shown by preparing various sulfated derivatives (FIG. 1) and testing them as cholesterol esterase inhibitors.

Compound 2

Sodium alginate (150 mg) was treated with glacial acetic acid (5 cc) for two hours at room temperature, filtered and resuspended in N,N-dimethylformamide (5 ml). To the stirred solution, sulfur trioxide-pyridine complex (1.5 g) was added over 30 minutes at room temperature and the resulting mixture was stirred overnight (16 hr). Dry pyridine (5 ml) was then added and the sulfated alginic acid was precipitated with 100 ml of acetone-methanol (9:1) mixture. The precipitate was dissolved iu H$_2$O (50 ml) and the pH of the solution was adjusted to pH 8 with 1 N NaOH. Re-precipitation with acetone-methanol (9:1) mixture (~200 ml) yielded the sodium salt of sulfated alginic acid. This compound was tested for cholesterol esterase inhibition as described above and it had an $IC_{50}$ of 0.25 µg/ml or 1.0 nM (FIG. 2).

Compound 5

Sodium alginate (1 g) was dissolved in 100 cc of deionized water, and 60 ml of 0.1 M bromine solution were added with stirring. The mixture was stirred at room temperature for 24 hr, and subsequently, the pH of the solution was adjusted to 8.0 with 1 N NaOH. After dialysis against water (6 liters×4) for 48 hours using 3,500 M.W. cut-off membrane, the solution was lyophilized to give 810 mg of oxidation product (Compound 3; FIG. 1).

To 575 mg of Compound 3 in water, 8 g of ammonium acetate and 8 g of sodium cyanoborohydride were added with stirring. The pH of the mixture was adjusted to 6.0 with 0.1 N HCl and stirring was continued at 40° C. for 48 hr. After cooling the mixture to room temperature, the pH of the solution was adjusted to 4.0 with 1 N HCl, and stirring was continued at room temperature for an additional 2 hrs. The reductive amination product was precipitated by adding absolute ethyl alcohol. This precipitate was dissolved in water (200 cc) and the pH was adjusted to 9 with 2 N NaOH solution. Treatment of this solution with 500 cc of ethyl alcohol-acetone (1:1) yielded a gelatin-type material which was collected by centrifugation. The resulting material was washed several times with absolute alcohol and acetone and lyophilized to yield 532 mg of the reduction product (Compound 4; FIG. 1).

Sulfation of Compound 4 was performed using sulfur trioxide pyridine complex by the method described earlier (see Compound 2). This sulfated alginic acid (Compound 5; FIG. 1) was tested for cholesterol esterase inhibition, and it had an $IC_{50}$ of 0.25 µg/ml or 0.10 nM (FIG. 2).

Compound 6

Oxidized alginic acid (500 mg; Compound 3) was treated with glacial acetic acid (25 ml) for 2 hr, the residue was suspended in DMF (25 ml) and 5 g of sulfur trioxide-pyridine complex were added over 30 min while the DMF solution stirred at 4° C. The reaction mixture was allowed to warm to room temperature and it was stirred for an additional 24 hr. Pyridine (25 ml) was added to the reaction mixture and the sulfated product was precipitated by adding acetone: methanol (9:1) to the solvent mixture (500 cc). The residue was dissolved in 60 ml of water and it was converted to the sodium salt by adjusting the pH of the solution to 8 with 1 N NaOH solution. The solution was dialyzed against water (4 liters×6) using 3,500 M.W. cut-off membrane over 48 hr and lyophilized to yield 520 mg of sulfated alginic acid (Compound 6; FIG. 1). This compound inhibited cholesterol esterase with an $IC_{50}$ of 0.06 µg/ml or 0.025 nM.

Compound 7

The sulfated alginic acid (Compound 7; FIG. 1) was prepared as described (Larm, 0., Larsson, K., Scholander, E., Andersson, L.G., Holmes, E. and Soderstrom, G., *Carbohydrate Research* 73:332, 1979). This compound inhibited cholesterol esterase with an $IC_{50}$ of 0.10 µg/ml or 0.42 nM.

All the sulfated derivatives of alginic acid are superior inhibitors when compared to the native polysaccharide. These results are tabulated below and show that sulfation enhances inhibition from 20 to 200-fold:

| Sample | IC$_{50}$ (nM) | Enhancement Factor |
| --- | --- | --- |
| Alginic Acid | 20.0 | 1.0 |
| Compound 2 | 1.0 | 20.0 |
| Compound 5 | 0.10 | 200.0 |
| Compound 6 | 0.25 | 80.0 |
| Compound 7 | 0.42 | 48.0 |

EXAMPLE III

Other common polysaccharides, when sulfated, also are potent inhibitors of cholesterol esterase.

Sulfated pectin was prepared by treating pectin (2 g) with glacial acetic acid, the polysaccharide was resuspended in N,N-dimethylformamide (25 ml), and the stirred suspension was cooled to 0° C. with an ice bath. Sulfur trioxide-pyridine complex (10 g, Aldrich) was added, and the temperature of the solution was allowed to reach room temperature. After stirring for an additional 3 hr, pyridine (20 ml) was added and the sulfated polysaccharide was precipitated with 95% ethyl alcohol (~300 ml). The precipitate was dissolved in water and the pH was adjusted to 7.5 with 1 N sodium hydroxide. Re-precipitation with 95% ethanol gave 1.8 g of the sodium salt of pectin sulfate. (Found: C. 34.53; H, 4.54., 0, 47.21; S, 0.77; Na, 8.31).

This compound was tested for cholesterol esterase inhibition and it had an IC$_{50}$ of 0.6 µg/ml or 30 nM (assuming a molecular weight of 20 kDa). Importantly, native, unsulfated pectin does not inhibit cholesterol esterase, demonstrating the importance of sulfation for effective inhibition.

Native pectin occurs naturally as the partial methyl ester of $\alpha(1\rightarrow 4)$ linked D-polygalacturonate sequences. The methyl ester was converted to the free acid by treatment with pectinesterase. Specifically, 1 g of pectin was dissolved in 100 ml of 0.1 M NaCl. The pH was adjusted to 7.5 and pectinesterase (1.4 mg, 250 Units, Sigma) was added. The pH of the reaction mixture was maintained at 7.5 with 0.1 N sodium hydroxide solution. When there was no further change in pH, about 2 hr., the solution was transferred to dialysis tubing and dialyzed against water overnight (4 liters×4) Lyophilization of the dialyzed solution gave 820 mg of hydrolyzed pectin. The methyl ester cleaved product was sulfated in a similar manner as described above for native pectin. This sulfated pectin inhibited cholesterol esterase with an IC$_{50}$ of 0.04 µg/ml or 2 nM.

Chitin, another naturally occurring polysaccharide, also contains potential sites for sulfation. Thus, 300 mg of chitin were treated with 5 ml of glacial acetic acid for 2 hr. at room temperature, and the insoluble chitin collected and resuspended in 10 ml of DMF. Sulfur trioxide-pyridine complex (3 g) was added at room temperature and the reaction mixture was stirred. After 80 hr., 5 ml of pyridine were added and the solution stirred for an additional 30 min. Sulfated chitin was precipitated by adding 95% ethyl alcohol (100 ml), and the solid was suspended in 100 cc of water and the pH of the solution was adjusted to 7.5. The chitin solution was then dialyzed against water for 48 hr. The solution was filtered and the clear filtrate was lyophilized to yield 48 mg of sulfated chitin. Chitin sulfate inhibited human cholesterol esterase with an IC$_{50}$ of 0.03 µg/ml or 0.06 nM (assuming a molecular weight of 300 kDa).

Since chitin is so insoluble, chitosan was used as starting material to increase the amount of sulfated material. Chitosan (1 g) was treated with 20 ml of glacial acetic acid for 2 hr at room temperature, and the residue was suspended in 25 ml of N,N-dimethylformamide. To this stirred solution, sulfur trioxide-pyridine complex (10 g) was added at room temperature. The resulting mixture was stirred for 2 hr and kept at room temperature for 72 hr. Pyridine (20 ml) was added and the sulfated chitosan was precipitated with acetone-methanol (9:1). It was then dissolved in 200 ml of water and the pH of the solution adjusted to 7.5 with 2 N sodium hydroxide solution. Re-precipitation with 95% ethyl alcohol gave the sodium salt of chitosan sulfate, which was redissolved in 200 ml of water. The polysaccharide solution was dialyzed against water (6 liters×4) for 48 hr and then lyophilized to give 1.12 g of the sodium salt of chitosan sulfate. When tested as an inhibitor of cholesterol esterase, it gave an IC$_{50}$ of 0.015 µg/ml or 0.03 nM.

Other commercially available, sulfated polysaccharides were also tested for inhibitory ability. Thus, cellulose sulfate (M.W.=500 kDa) had an IC$_{50}$ of 0.02 nM and dextran sulfate also had an IC$_{50}$ of 0.02 nM. The IC$_{50}$'s for all these sulfated compounds are summarized below:

| Compound | IC$_{50}$ (nM) |
| --- | --- |
| Pectin Sulfate | 30.0 |
| Pectin (Hydrolyzed) Sulfate | 2.0 |
| Chitin Sulfate | 0.06 |
| Chitosan Sulfate | 0.03 |
| Cellulose Sulfate | 0.02 |
| Dextran Sulfate[a] | 0.02 |
| Dextran Sulfate[b] | 20.0 |

[a]Dextran Sulfate of molecular weight 500,000
[b]Dextran Sulfate of molecular weight 5000.

In addition, amylopectin sulfate, prepared as described below, acts as an inhibitor of cholesterol esterase.

Into a jacketed reaction vessel equipped with means for mechanical agitation and containing 1,100 parts of softened water (deionized, distilled, or tap water may also be used) 275 parts of amylopectin fractionated from potato starch was added, with stirring. After 30 minutes agitation, the pH was adjusted to about 10.5–11.0 with portions of a 25%, by weight, aqueous NaOH solution. The temperature was 80° F.

Six hundred and twenty parts of a trimethylamine-sulfur trioxide complex were slowly added over a period of one and a half hours. Simultaneously, more of the 25% NaOH solution was introduced by means of a programmed addition designed to maintain the pH at 11.0. This programmed addition was maintained throughout the entire reaction.

After all the trimethylamine-sulfur trioxide addition product was added, the vessel was closed and a vacuum of 12" water was applied in order to initiate the removal of some of the trimethylamine which was being formed during the reaction. At the same time the temperature was slowly raised to 122° F. over a period of one and a half hours with continuing programmed additions of caustic. After 11 hours at 122° F., with caustic additions programmed to keep the pH at 11.0, the reaction was completed.

The vacuum was then raised to 27" mercury and the trimethylamine was removed by stripping while the pH was maintained at 11 through the programmed addition of the 25% NaOH solution. After the bulk of the trimethylamine was removed, water stripping was started using 1150 parts of water while keeping the pH at about 11.

The free trimethylamine content was reduced to below 100 p.p.m. after which the vacuum was removed and the solids adjusted to a level of 25%, by weight, and the pH to 10.8-11.0. The resulting solution was then dialyzed continuously against soft water, using parchment as a membrane to a salt content of 5% $Na_2SO_4$ based on the starch solids.

The pH at this stage was about 8. The product was then spray dried using an inlet temperature of 450° F., and an outlet temperature of 210° F.

The resulting spray dried amylopectin sulfate was in the form of a white powder and entirely devoid of any odor or taste resulting from the presence of any residual traces of unreacted trimethylamine.

EXAMPLE IV

The sulfated polysaccharides described here also inhibit the hydrolysis of triolein by the human 100 kDa cholesterol esterase. (The same assay procedure was used as described in Part I, only triolein was used instead of cholesteryl oleate.) As shown in the table below, the $IC_{50}$ for inhibition of triolein hydrolysis is nearly the same as that for cholesteryl oleate hydrolysis. These data indicate that these compounds are also useful agents for blocking the uptake of fats, as well as the uptake of cholesterol.

| Compound | $IC_{50}$ (nM) Triolein | Cholesteryl Oleate |
|---|---|---|
| Alginic Acid | 42.0 | 20.0 |
| Compound 2 | 3.3 | 1.0 |
| Compound 5 | 0.25 | 0.10 |
| Compound 6 | 0.83 | 0.25 |
| Compound 7 | 0.42 | 0.42 |
| Pectin Sulfate | 25.0 | 30.0 |
| Pectin (Hydrolyzed Sulfate) | 2.5 | 2.0 |
| Chitin Sulfate | 0.14 | 0.06 |
| Chitosan Sulfate | 0.16 | 0.03 |
| Cellulose Sulfate | 0.06 | 0.02 |
| Dextran Sulfate | 0.08 | 0.02 |

EXAMPLE V

The sulfated polysaccharides described here retain their inhibitory activity for prolonged periods at elevated temperatures. This property allows them to be stable under baking conditions and provides a convenient vehicle for their administration. For example, 109 mg of cellulose sulfate were added to 198 gm (7 oz) of corn muffin mix (Gold Medal ®) and the solid ingredients were thoroughly mixed together. After the addition of one egg and one-third cup milk, the muffin mix was stirred fifteen times. The mixture was poured into nine muffin tins and baked for fifteen minutes in a 400° oven. The next day one muffin was broken up, added to 100 ml of water and allowed to stand for fifteen minutes. The mixture was centrifuged and the clear supernatant was assayed for the presence of cholesterol esterase inhibition. The $IC_{50}$ of this solution was achieved when this solution was diluted $10^3$-$10^4$ times. These data indicate that the inhibitor is stable under baking conditions and that it can be released into solution from baked goods.

EXAMPLE VI

Sulfated agar was prepared from commercial agar by first suspending 2g of commercial agar in N,N-dimethylformamide (25 ml), and cooling the stirred suspension to 0° C. with an ice bath. Sulfur trioxide-pyridine complex (10 g, Aldrich) was added, and the temperature of the solution was allowed to reach room temperature. After stirring for an additional 3 hr, pyridine (20 ml) was added and the sulfated polysaccharide was precipitated with 95% ethyl alcohol ($\sim$300 ml). The precipitate was dissolved in water and the pH was adjusted to 7.5 with 1 N sodium hydroxide. Reprecipitation with 95% ethyl alcohol gave sulfated agar.

Human pancreatic cholesterol esterase was purified as described by Bosner et al., *Proc. Natl. Acad. Sci.*, 85, 7438 (1988). To measure pancreatic cholesterol esterase inhibition by sulfated agar, 50 $\mu$l of pancreatic cholesterol esterase (10 $\mu$g/ml), 75 $\mu$l of phosphatidylcholine vesicles containing cholesteryl $^{14}C$-oleate (1 mM 2,000 CPM/nmole), 25 $\mu$l of 100 mM taurocholate, 120 $\mu$l of 150 mM Tris, pH 7.5 and 30 $\mu$l of test sulfated agar solution were incubated at 37° C. for fifteen minutes. The assay was quenched by placing the reaction vessels in a 4° C. ice bath and by adding 0.6 ml of 0.3 N NaOH and 3 ml of benzene/chloroform/methanol (1.0/1.2/0.5). The quenched reactions were vortexed for 30 seconds, centrifuged at 3,000 g for 15 minutes and 1 ml of the upper aqueous phase was added to 7 ml of Aquasol-2 (DuPont) with 0.025 ml of 6 N HCl. These mixtures were vortexed for one minute and counted for $^{14}C$-oleate. The counts were compared to a sample which contained cholesterol esterase but no sulfated agar to determine the percentage of inhibition.

Following this assay procedure, sulfated agar was determined to have an $IC_{50}$ toward human pancreatic cholesterol esterase of less than $3.3 \times 10^{-11}$M, or 0.033 nM (based on a molecular weight of 300 kDa).

The $IC_{50}$ was determined for native (unsulfated) agar to be $3 \times 10^{8}$M, or 30 nM. This inhibition may be due to contamination of agar by agaropectin, a sulfated form of agar found in most commercial preparations of agar.

EXAMPLE VII

Figure 3:
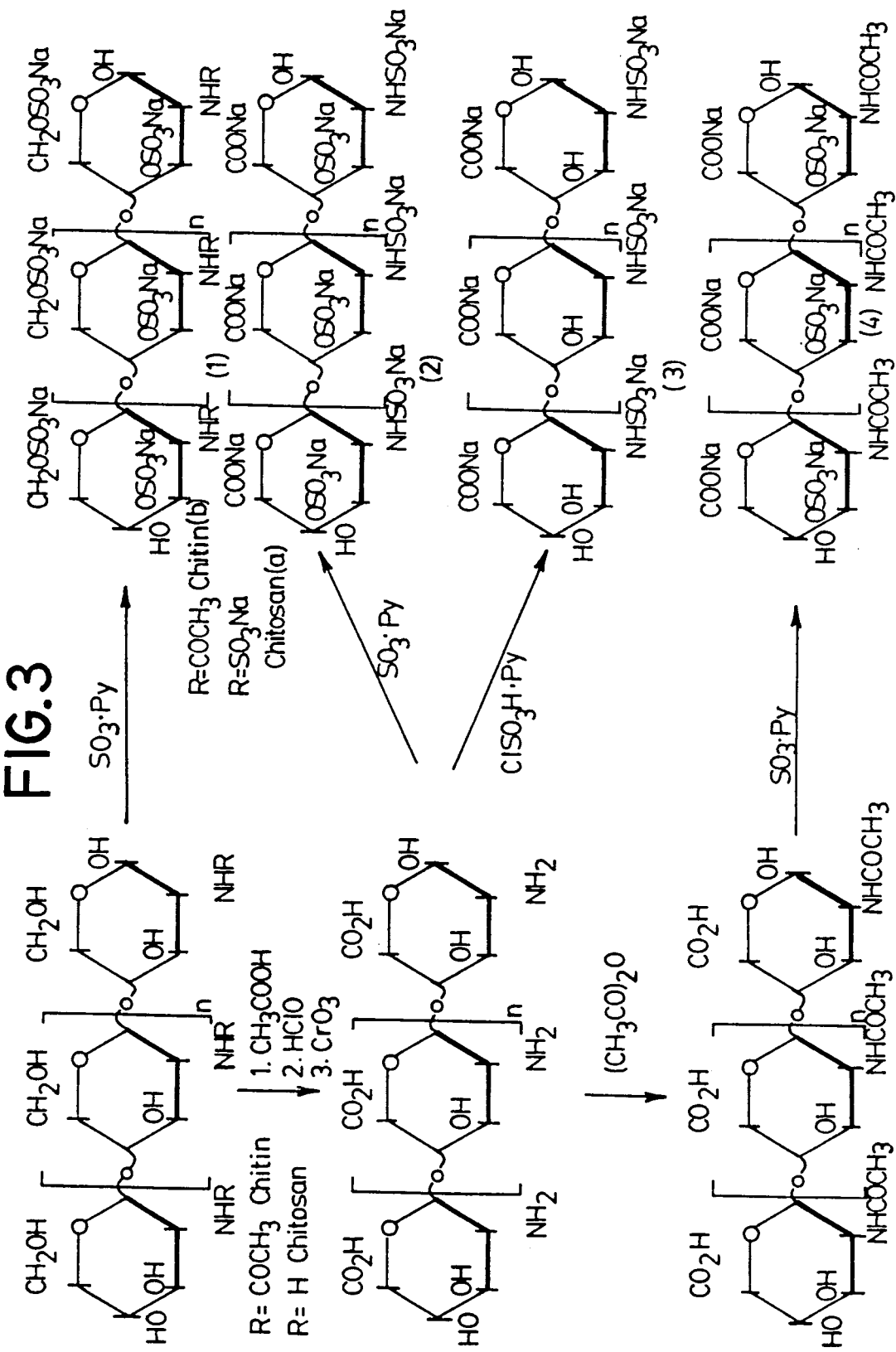
FIG. 3. The synthetic strategy employed for preparing several sulfated chitin and chitosan derivatives.

The structural basis for the potent inhibition of human pancreatic cholesterol esterase exhibited by chitosan (0.03 nM, Example III) was determined by preparing a number of chitosan derivatives sulfated at various positions on the polysaccharide ring. Five different compounds were synthesized using the strategy outlined in FIG. 3, and their inhibitory activity was determined in the assay described in Example VI, above. The structure activity relationships for the five sulfated polysaccharides is summarized below.

As the data demonstrates, the presence of 3-sulfate is both necessary and sufficient to produce inhibitory activity by these polysaccharides toward human pancreatic cholesterol esterase. However, sulfation at the 2-position decrease activity while 6-sulfation is unnecessary.

| COMPOUND | SULFATION POSITION $2^a$ | $3^b$ | $6^b$ | $IC_{50}$ |
|---|---|---|---|---|
| Ia | + | + | + | $8 \times 10^{-3}$ |
| Ib | − | + | + | $1 \times 10^{-4}$ |
| II | + | + | − | $8 \times 10^{-4}$ |
| III | + | − | − | N.I. |

-continued

| COMPOUND | SULFATION POSITION | | | |
|---|---|---|---|---|
| | $2^a$ | $3^b$ | $6^b$ | $IC_{50}$ |
| IV | − | + | − | $1 \times 10^{-4}$ |

$^a$Position 2 is N-sulfation;
$^b$positions 3 & 6 are O-sulfation.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method for inhibiting human pancreatic cholesterol esterase comprising contacting the human pancreatic cholesterol esterase with an effective inhibiting amount of a 3-sulfate polysaccharide having a molecular weight greater than 10,000 Daltons.

2. A method according to claim 1 wherein the 3-sulfate polysaccharide has a molecular weight greater than 100,000 daltons.

3. A method according to claim 2 wherein the 3-sulfate polysaccharide has a molecular weight greater than 500,000 Daltons.

4. A method according to claim 1 wherein the 3-sulfated polysaccharide is selected from the group consisting of 3-sulfated alginic acid, pectin, amylopectin, chitin, dextran, cellulose, agar, or chitosan.

* * * * *